US011311579B2

United States Patent
Shimohata et al.

(10) Patent No.: US 11,311,579 B2
(45) Date of Patent: Apr. 26, 2022

(54) CELL PREPARATION AND METHOD FOR PRODUCING CELL PREPARATION

(71) Applicant: NIIGATA UNIVERSITY, Niigata (JP)

(72) Inventors: Takayoshi Shimohata, Niigata (JP); Masato Kanazawa, Niigata (JP)

(73) Assignee: NIIGATA UNIVERSITY, Niigata (JP)

( * ) Notice: Subject to any disclaimer, the term of this patent is extended or adjusted under 35 U.S.C. 154(b) by 280 days.

(21) Appl. No.: 16/329,039

(22) PCT Filed: Aug. 30, 2017

(86) PCT No.: PCT/JP2017/031246
§ 371 (c)(1),
(2) Date: Feb. 27, 2019

(87) PCT Pub. No.: WO2018/043596
PCT Pub. Date: Mar. 8, 2018

(65) Prior Publication Data
US 2019/0216856 A1    Jul. 18, 2019

(30) Foreign Application Priority Data

Aug. 30, 2016 (JP) .............................. JP2016-168543

(51) Int. Cl.
| | |
|---|---|
| *A61K 35/30* | (2015.01) |
| *A61K 35/15* | (2015.01) |
| *A61P 9/10* | (2006.01) |
| *C12N 5/00* | (2006.01) |
| *C12N 5/079* | (2010.01) |
| *C12N 5/0786* | (2010.01) |
| *A61K 9/10* | (2006.01) |
| *A61P 43/00* | (2006.01) |

(52) U.S. Cl.
CPC ................ *A61K 35/30* (2013.01); *A61K 9/10* (2013.01); *A61K 35/15* (2013.01); *A61P 9/10* (2018.01); *A61P 43/00* (2018.01); *C12N 5/0018* (2013.01); *C12N 5/0622* (2013.01); *C12N 5/0645* (2013.01); *C12N 2500/02* (2013.01); *C12N 2500/34* (2013.01)

(58) Field of Classification Search
None
See application file for complete search history.

(56) References Cited

U.S. PATENT DOCUMENTS

2012/0100610 A1    4/2012  Mizukami et al.

FOREIGN PATENT DOCUMENTS

| WO | WO 2009/034708 A1 | 3/2009 |
| WO | WO 2010/116665 A1 | 10/2010 |
| WO | WO 2016/068217 A1 | 5/2016 |

OTHER PUBLICATIONS

Del Zoppo GJ, Frankowski H, Gu YH, et al. Microglial cell activation is a source of metalloproteinase generation during hemorrhagic transformation. J Cereb Blood Flow Metab. 2012;32(5):919-932. doi:10.1038/jcbfm.2012.11 (Year: 2012).*
Hu X, Leak RK, Shi Y, Suenaga J, Gao Y, Zheng P, Chen J. Microglial and macrophage polarization—new prospects for brain repair. Nat Rev Neurol. Jan. 2015;11(1):56-64 (Year: 2015).*
Barakat R, Redzic Z. Differential cytokine expression by brain microglia/macrophages in primary culture after oxygen glucose deprivation and their protective effects on astrocytes during anoxia. Fluids Barriers CNS. Feb. 28, 2015;12:6 (Year: 2015).*
Fuss IJ, Kanof ME, Smith PD, Zola H. Isolation of whole mononuclear cells from peripheral blood and cord blood. Curr Protoc Immunol. Apr. 2009;Chapter 7:Unit7.1. (Year: 2009).*
Rodriguez-Frutos, B., Otero-Ortega, L., Gutiérrez-Fernández, M. et al. Stem Cell Therapy and Administration Routes After Stroke. Transl. Stroke Res. Epub Jul. 7, 2016: 7, 378-387 (2016). (Year: 2016).*
International Search Report dated Dec. 5, 2017 in PCT/JP2017/031246, citing documents AA, AO, AP and AAA-AAH therein, 3 pages.
English translation of the International Preliminary Report on Patentability dated Jan. 31, 2019 in PCT/JP2017/031246 filed Aug. 30, 2017, citing documents AA, AO, AAB, and AAH-AAJ therein, 9 pages.
Extended European Search Report dated Feb. 13, 2020 in Patent Application No. 17846600.9, citing documents AAK-AAM therein, 8 pages.
Elizabeth Guida, et al., "Influence of Hypoxia and Glucose Deprivation on Tumour Necrosis Factor-Alpha and Granulocyte-Macrophage Colony-Stimulating Factor Expression in Human Cultured Monocytes" Cellular Physiology and Biochemistry, vol. 8, 1998, pp. 75-88 and cover pages.
Malgorzata Ziemka-Nalecz, et al., "Oxygen-Glucose Deprivation Promotes Gliogenesis and Microglia Activation in Organotypic Hippocampal Slice Culture: Involvement of Metalloproteinases" Acta Neurobiologiae Experimentalis, vol. 73, 2013, pp. 130-142.
Zoran B. Redzic, et al., Differential Effects of Paracrine Factors on the Survival of Cells of the Neurovascular Unit During Oxygen Glucose Deprivation, International Journal of Stroke, vol. 10, Apr. 2015, pp. 407-414.
Umadevi V. Wesley, et al., "Galectin-3 Enhances Angiogenic and Migratory Potential of Microglial Cells Via Modulation of Integrin Linked Kinase Signaling" Brain Res., vol. 1496, 2014, pp. 1-9.

(Continued)

*Primary Examiner* — Ram R Shukla
*Assistant Examiner* — Austin Jeffries
(74) *Attorney, Agent, or Firm* — Oblon, McClelland, Maier & Neustadt, L.L.P.

(57) ABSTRACT

The present invention provides a method for producing a cell culture for promoting angiogenesis or axon outgrowth, particularly for the treatment of a cerebrovascular disease, an ischemic cardiac disease or traumatic brain injury and spinal cord injury, which comprises culturing a cell population containing microglia and/or monocytes under conditions of low oxygen concentration and/or low sugar concentration to produce the culture, a cell preparation obtained by the method, and a method for treating a cerebrovascular disease, an ischemic cardiac disease or traumatic cerebrospinal neuropathy by using the cell preparation.

12 Claims, 9 Drawing Sheets

(56) References Cited

OTHER PUBLICATIONS

Takayoshi Shimohata, et al., "Multiple Therapeutic Effects of a Growth Factor, Progranulin on Ischemic Brain Injury, Cerebral Blood Flow and Metabolism" Department of Neurology, Brain Research Institute, Niigata University 2016, vol. 27, pp. 265-269 (with English Abstract).

Ya-Chi Huang, et al., "The Good and Bad Microglia/Macrophages: New Hope in Stroke Therapeutics" Acta Pharmacologica Sinica, vol. 34, 2013, pp. 6-7.

Fumihiro Imai, et al., "Neuroprotective Effect of Exogenous Microglia in Global Brain Ischemia" Journal of Cerebral Blood Flow & Metabolism, vol. 27, 2007, pp. 488-500.

Mayumi Egawa, et al., "Inflammatory Monocytes Recruited to Allergic Skin Acquire an Anti-inflammatory M2 Phenotype Via Basophil-Derived Interleukin-4" Cell Press, vol. 38, Mar. 21, 2013, pp. 570-580.

Ektoras Hadjipanayi, et al., "Hypoxia-Based Strategies for Angiogenic Induction: The Dawn of a New Era for ischemia Therapy and Tissue Regeneration" Organogenesis, XP055664816, vol. 9, No. 4, Oct. 1, 2013, pp. 261-272.

Tomoaki Kudo, et al., "Original Article Hypoxically Preconditioned Human Peripheral Blood Mononuclear Cells Improve Blood Flow in Hindlimb Ischemia Xenograft Model", Am J Transl Res, XP055664809, vol. 6, No. 5, Jan. 1, 2014, pp. 570-579.

Masayuki Kubo, et al., "Hypoxic Preconditioning Increases Survival and Angiogenic Potency of Peripheral Blood Mononuclear Cells Via Oxidative Stress Resistance", American Journal of Physiology: Heart and Circulatory Physiology, XP055664806, vol. 294, No. 2, Feb. 1, 2008, pp. H590-H595.

Somsak Wattananit, et al. "Monocyte-Derived Macrophages Contribute to Spontaneous Long-Term Functional Recovery after Stroke in Mice" The Journal of Neuroscience, vol. 36, No. 15, Apr. 13, 2016, pp. 4182-4195.

Virginie Desestret, "In Vitro and In Vivo Models of Cerebral Ischemia Show Discrepancy in Therapeutic Effects of M2 Macrophages". PLoS One, Jun. 2013, vol. 8, Issue 6, 12 pages.

Ewa Zajac, "Angiogenic capacity of M1- and M2-polarized macrophages is determined by the levels of TIMP-1 complexed with their secreted proMMP-9", The American Society of Hematology (2013), Blood, Dec. 12, 2013, vol. 122. No. 25, 14 pages.

* cited by examiner

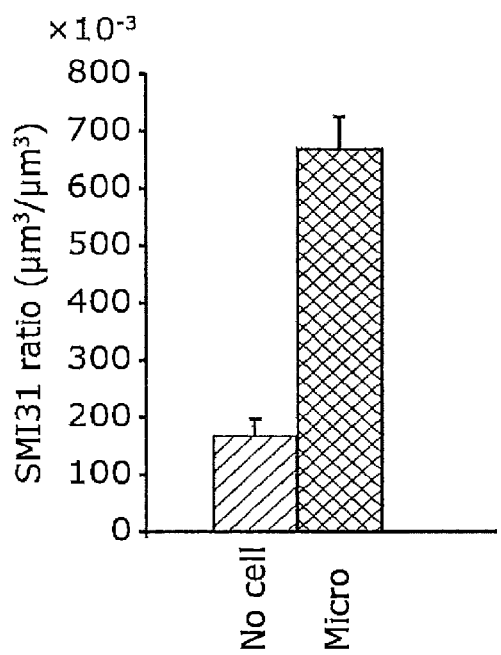
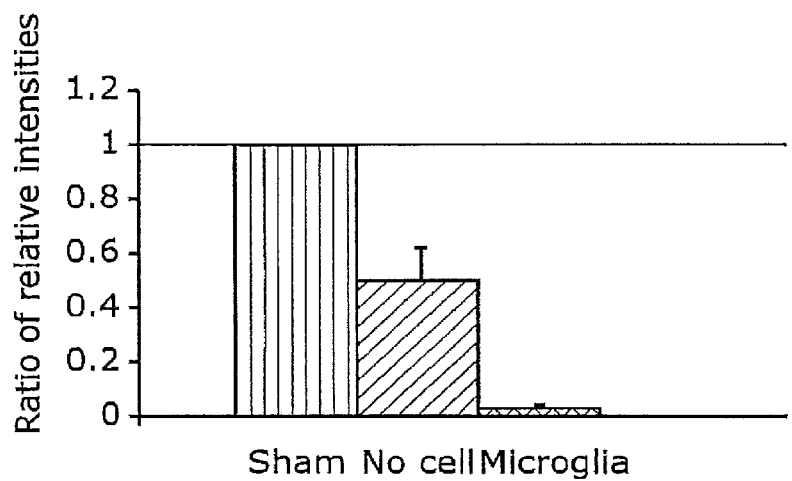

Fig. 17
(A)
human-derived PMNCs
WB of cells
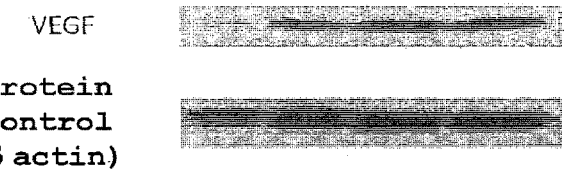
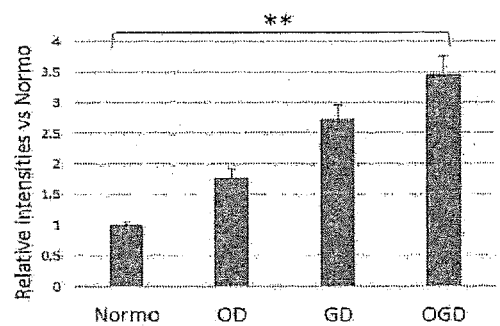
WB of medium
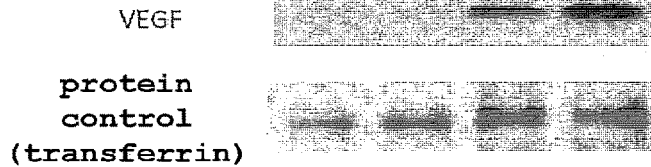
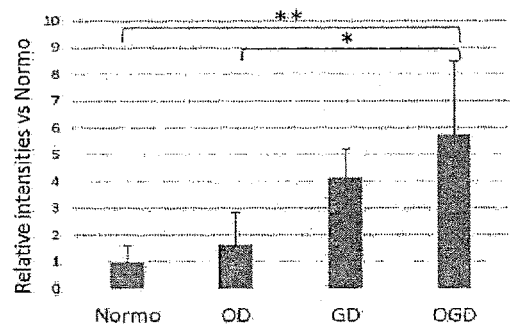
(B)
human-derived PMNC — medium of cell ELISA
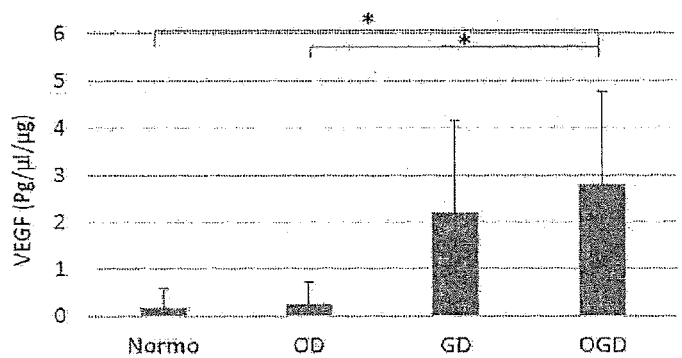
N (normo): normal state
OD: oxygen deprivation
GD: glucose deprivation
OGD: oxygen-glucose deprivation

CELL PREPARATION AND METHOD FOR PRODUCING CELL PREPARATION

TECHNICAL FIELD

The present invention relates to a cell preparation effective for repair and regeneration of a tissue damaged by, for example, cerebral infarction and the like and a production method thereof and the like.

BACKGROUND ART

Cerebral infarction refers to brain dysfunction caused by ischemic necrosis of the brain locus, is a disease requiring emergency treatment, and is one of the three major causes of death along with cancer and heart disease. Cerebral infarctions are classified as thrombotic, embolic, or hemodynamic in terms of action mechanism, and are classified as atherothrombotic cerebral infarction, cardiogenic embolism, or lacunar infarction in terms of clinical findings.

Ischemia is caused by blocking of local cerebral blood flow due to cerebrovascular lesions such as arteriosclerosis, or cardiogenic thrombus, and neuronal cell death is caused by energy depletion in the ischemic core. After ischemia, nerve regeneration is poor, and recovery of symptoms in the chronic stage is difficult at present, and half of patients suffer from some sequelae. It is assumed that revascularization triggers the process of nerve regeneration at the marginal region of the ischemic core. The development of a treatment method targeting such nerve regeneration process has been desired.

Various attempts have been made relating to the treatment of cerebral infarction. However, they are not sufficient and treatment methods using living cells have been attempted in recent years (patent documents 1 and 2, and non-patent document 1).

Patent document 1 describes a method for obtaining cells containing mesenchymal stem cells collected from bone marrow or blood, without using an anticoagulant such as heparin, and using the cells to treat diseases such as cerebral infarction and the like. Patent document 2 describes a treatment method of cerebral infarction with MUSE cells.

In addition, intravenous administration of bone marrow-derived monocytes (CD115 positive cells) to a mouse cerebral infarction model has been confirmed to cause transfer of these cells to infarct area and the effect thereof was confirmed; however, the effect was not sufficient (non-patent document 1).

DOCUMENT LIST

Patent Documents patent document 1: WO 2009/034708
patent document 2: JP-A-2015-159895

Non-Patent Document non-patent document 1: Somsak Wattananit "Monocyte-Derived Macrophages Contribute to Spontaneous Long-Term Functional Recovery after Stroke in Mice" The Journal of Neuroscience, 13 Apr. 2016, 36(15): 4182-4195; doi: 10.1523/JNEUROSCI.4317-15.2016

SUMMARY OF THE INVENTION

Problems to be Solved by the Invention

However, the cell preparations described in the above-mentioned patent documents 1 and 2 require collection of the bone marrow fluid, which places a heavy burden on the patients. Also, obtainment of mesenchymal stem cells problematically requires long-term culture. By the administration of bone marrow-derived monocytes as described in non-patent document 1, moreover, transfer to the infarct region could be confirmed but a problem has occurred that a therapeutic effect on cerebral infarction and the like is insufficient.

The problem of the present invention is to solve the aforementioned conventional problems and achieve the following object. That is, the present invention aims to provide a cell preparation and a production method thereof, which are less burdensome to patients, have high safety, and are highly effective in treating cerebral infarction.

Means of Solving the Problems

The present inventors have found that administration of microglia or mononuclear cells containing monocytes treated with oxygen-glucose deprivation (OGD) prevents deterioration after the onset of cerebral infarction and cerebral infarction is treated by promoting angiogenesis and axon outgrowth, which resulted in the completion of the present invention.

Accordingly, the present invention provides the following.

<1> The present invention is a method for producing a cell culture for the treatment of a disease selected from ischemic cerebrovascular disease, myocardial infarction, cerebral hemorrhage, and traumatic brain injury and spinal cord injury, comprising culturing a cell population containing microglia and/or monocytes under conditions of low oxygen concentration and/or low sugar concentration.

<1a> The present invention is a method for producing a cell culture for the promotion of angiogenesis or axon outgrowth, comprising culturing a cell population containing microglia and/or monocytes under conditions of low oxygen concentration and/or low sugar concentration.

<2> In any of the aforementioned methods, the cell population is preferably cultured at least under conditions of low sugar concentration.

<3> In any of the aforementioned methods, the cell population is preferably cultured in a basal medium.

<4> For example, the aforementioned cell population containing monocytes is peripheral blood cells or a fraction thereof.

<4a> Alternatively, the aforementioned cell population containing monocytes is a fraction containing mononuclear cells collected from the peripheral blood.

<5> In addition, the low oxygen concentration may be an oxygen concentration of less than 1%.

<6> In addition, the low sugar concentration may be a sugar concentration of not more than 1.0 g/L.

<7> In addition, in the aforementioned production of the culture, the aforementioned cell population may be cultured under conditions of low oxygen concentration and low sugar concentration for less than 24 hr.

<8> In the aforementioned production of the cell preparation, the aforementioned produced culture may be further washed and the washed culture may be enclosed in a vessel.

<9> The present invention is a cell preparation for the treatment of a disease selected from ischemic cerebrovascular disease, myocardial infarction, cerebral hemorrhage and traumatic brain injury and spinal cord injury, the preparation comprising microglia and/or monocyte having ability to promote angiogenesis and/or axon outgrowth sufficient for the treatment of a disease selected from ischemic cerebrovascular disease, myocardial infarction, cerebral hemorrhage, and traumatic brain injury and spinal cord injury.

<9a> The present invention is a cell preparation for the treatment of a disease selected from ischemic cerebrovascular disease, myocardial infarction, cerebral hemorrhage, and traumatic brain injury and spinal cord injury, the preparation comprising a culture produced by culturing a cell population containing microglia and/or monocytes under conditions of low oxygen concentration and/or low sugar concentration.

<10> The present invention is a cell preparation for promoting angiogenesis or axon outgrowth, the preparation comprising a culture produced by culturing a cell population containing microglia and/or monocytes under conditions of low oxygen concentration and/or low sugar concentration.

<11> The present invention is a method for treating a disease selected from ischemic cerebrovascular disease, myocardial infarction, cerebral hemorrhage, and traumatic brain injury and spinal cord injury, the method comprising administering to a subject a culture containing a therapeutically effective amount of microglia and/or monocytes and produced by culturing a cell population containing microglia and/or monocytes under conditions of low oxygen concentration and/or low sugar concentration.

Effect of the Invention

According to the present invention, by merely culturing microglia or monocytes for a very short period of time under conditions of low oxygen concentration and/or low sugar concentration, the ability to promote angiogenesis and axon outgrowth can be imparted to the cells, and therefore, ischemic cerebrovascular disease and myocardial infarction can be treated from the early stage of the onset. Moreover, the present invention is widely available in general medical institutions because there are no limits on implementation in cell processing centers (CPCs) as in the case of mesenchymal stem cells or bone marrow stem cells. In addition, since serum, growth factor or the like is not required for culturing, cell preparations can be provided safely at a low cost.

Furthermore, when a cell population containing monocytes derived from peripheral blood is used, it is not necessary to collect the bone marrow fluid, so that the burden on the patient in the treatment of cerebral infarction can be reduced and safety can be enhanced.

In the case of a patient with cerebral hemorrhage or cerebrospinal trauma, microglia can be easily collected from the destroyed white matter around the hematoma after the hematoma removal surgery, and therefore, the aforementioned disease can be treated by applying the present invention to microglia directly collected from the brain or spinal cord of the patient.

In addition, since culturing is performed under conditions of low oxygen concentration and/or low sugar concentration, angiogenesis and axon outgrowth can be promoted more, and the therapeutic effect can be enhanced.

BRIEF DESCRIPTION OF THE DRAWINGS

FIG. 9 shows immunoreactivity against SMI31 (volume per unit volume).

FIG. 10 shows relative intensity of chondroitin sulfate proteoglycan/neuron glial antigen 2 (CSPG/NG2) from cerebral cortex in rats on day 28 after ischemia and before ischemia.

FIG. 17 shows the effects of stimulation by oxygen deprivation (OD), stimulation by glucose deprivation (GD) or stimulation by oxygen-glucose depletion (OGD) on production (A) and secretion (B) of VEGF in human PMNCs. (A) Western blot images of cell extract (upper panel) and culture supernatant (lower panel) after each stimulation (left) and a graph of relative band intensity of VEGF (right). (B) A graph showing the results of ELISA for the culture supernatant after each stimulation. In the Figure, "**" shows $p<0.01$, and "*" shows $p<0.05$.

Figure 1:
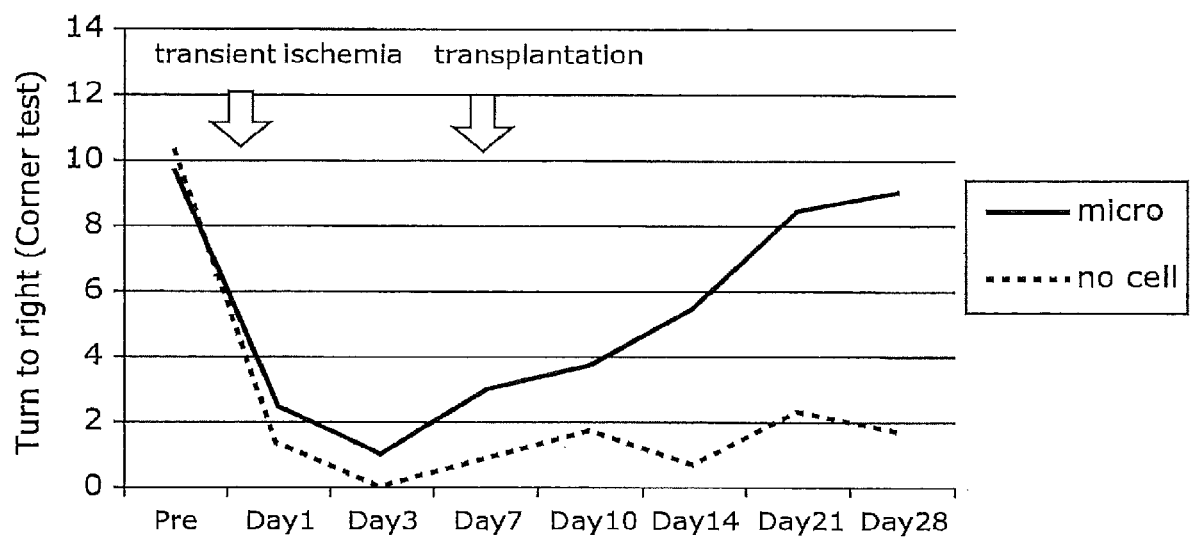
FIG. 1 shows one example of the improved results of neurological outcome in rat model of transient focal cerebral ischemia after transplantation of OGD pre-treated microglia.

DESCRIPTION OF EMBODIMENTS (Finding as the Basis of the Present Invention)

More than half of the survivors of ischemic stroke patients suffer from motor dysfunction. Therefore, it is necessary to establish a method for promoting functional recovery in stroke patients in sub-acute and chronic stages. Although various approaches have been taken to develop a therapeutic drug, a sufficient therapeutic drug is not available at present, and physical rehabilitation remains the only therapeutic option for promoting functional recovery in ischemic stroke patients.

Cell therapy using bone marrow mononuclear cell or bone marrow-derived mesenchymal stem cell/stromal cell may be another treatment method for promoting functional recovery in stroke patients in the sub-acute and chronic stages. One of the mechanisms of cell-based treatments using neural progenitor cell, bone marrow stromal cell and mesenchymal stem cell induces angiogenesis through secretion of VEGF or brain-derived neurotrophic factor (BDNF). Axon outgrowth after cell therapy has also been reported. However, a recent, multi-randomized, controlled trial has demonstrated no beneficial effect of intravenous administration of bone marrow mononuclear stem cells on ischemic stroke. Also, since patients with ischemic stroke receive anticoagulant or antiplatelet therapy to prevent recurrence, it is technically difficult to harvest stem cells from the bone marrow. Bone marrow-derived cells may not penetrate the blood-brain barrier (BBB) and may not migrate into the brain.

Thus, the present inventors considered that cell therapy using microglia may be another promising treatment method, since microglial cell is the primary source of the above-mentioned growth factor in the central nervous system (CNS). Several previous studies have demonstrated that microglia expands cerebral infarction volume in the acute stage, whereas microglia after cerebral ischemia in the sub-acute and chronic stages is known to play a protective role through tissue and vascular remodeling.

This protective microglia is called M2 microglia, and the protection effect thereof is considered to be triggered by secretion of remodeling factors such as VEGF and BDNF that can promote angiogenesis and axon outgrowth after cerebral ischemia, matrix metalloproteinase-9 (MMP-9), transforming growth factor β (TGF-β) and the like. In addition, transplanted microglia can migrate into the brain through BBB, particularly in the cerebral ischemic state.

It is also known that monocytes in the blood migrate into the brain and differentiate into microglia.

Based on the above-mentioned findings, the present inventors assumed that microglia or monocyte preconditioned with OGD and administered peripherally migrates through BBB into the brain parenchyma, secretes remodeling factors, and can exert multifaceted therapeutic effects through promotion of angiogenesis and axonal outgrowth for focal cerebral ischemia in the sub-acute stage.

To verify the assumption, the present inventors administered microglia or peripheral blood mononuclear cells (PMNCs) treated with OGD to a rat model of transient focal cerebral ischemia and found that the microglia or monocyte migrates through BBB into the brain and promotes functional recovery of the brain through promotion of angiogenesis and axonal outgrowth.

The present inventors also compared production amount and secretion amount of VEGF which is a humoral factor for the angiogenesis in the cell population between treatment of human PMNCs with OGD and stimulation with either oxygen depletion (OD) or glucose depletion (GD). As a result, it was clarified that the production amount of VEGF is higher in the order of OGD treatment, GD treatment, OD treatment than that without stimulation and the secretion amount of VEGF is remarkably high with OGD treatment or GD treatment as compared to that with OD treatment.

The present invention provides a production method of a cell culture for the promotion of angiogenesis or promotion of axon outgrowth, particularly, the aforementioned culture for the treatment of ischemic cerebrovascular diseases (cerebral infarction) such as cerebral thrombus, cerebral infarction and the like, or hemorrhagic cerebral disorders (cerebral hemorrhage) such as intracerebral bleeding, subarachnoid hemorrhage and the like, ischemic cardiac diseases such as myocardial infarction and the like, or traumatic brain injury and spinal cord injury (hereinafter to be also referred to as "the production method of the present invention"). The method includes producing the aforementioned culture by culturing a cell population containing microglia and/or monocytes under conditions of low oxygen concentration and/or low sugar concentration.

The cell population used in the production method of the present invention contains is not particularly limited as to its derivation as long as it contains microglia or monocytes, and is appropriately collected from human or other mammal (e.g., mouse, rat, dog, cat, monkey, bovine, swine and the like). As for cells containing microglia, for example, nerve tissue such as cerebrum or the like is dispersed and cultured in an adherent cell culture vessel using a serum-added culture solution. As a result, glial cells, mainly astrocytes, proliferate to form a monolayer on the surface of the culture vessel. After this, the proliferation state of microglia is readily recognized. A microglial culture test system can be made by collecting and culturing the microglia. When collecting the cells, a method of shaking the culture vessel is often used. This includes addition of a physical stimulation to liberate microglia adhered on the monolayer astrocyte cultured cells, and more cells can be collected. Microglia can also be purified directly from a dispersion of a neural tissue such as cerebrum or the like, or microglial cell fraction obtained by the above-mentioned method can also be purified by MACS or FACS using anti-CD115 antibody with CD115 as an index. It can also be obtained by differentiation from progenitor cell or stem cell such as monocyte, hematopoietic stem cell and the like.

In application to a human, for example, in a patient requiring surgical operation due to cerebral hemorrhage or brain trauma, after hematoma removal, the destroyed white matter around hematoma can be excised using a neuroendoscope, and microglia migrated into the white matter can be isolated and used. Although collection of microglia from human is highly invasive and inherently difficult, it is sufficiently tolerated in the above case because destroyed white matter to be necessarily obtained by surgery is used as the source.

As the cell population containing monocytes, a bone marrow-derived mononuclear cell fraction or peripheral blood-derived mononuclear cell fraction obtained by a known method can be used. In consideration of minimal invasiveness and, in the case of ischemic diseases, difficulty in collecting bone marrow fluid since an anticoagulant/antithrombotic therapy is generally carried out to prevent recurrence, a peripheral blood-derived mononuclear cell fraction is more preferable. The mononuclear cell fraction can be separated and purified from a bone marrow fluid or peripheral blood, for example, by Ficoll density gradient centrifugation by a method known per se. Furthermore, for example, monocytes can also be generated and used by MACS or FACS using anti-CD14 antibody. Monocytes can also be used by differentiating from hematopoietic stem cells or pluripotent stem cells.

The oxygen-glucose depletion treatment (OGD treatment) in the present invention refers to a treatment by culturing the above-mentioned cell population in a medium under low oxygen and low sugar conditions compared to normal culture conditions. While the OGD treatment conditions are appropriately selected according to the kind of the cell population containing the microglia or monocytes used in the present invention, they can be selected using the production amounts of VEGF, TGF-β, MMP-9 as an index and around the conditions under which the expression levels thereof are maximized. For example, in a CD115-positive rat microglia fraction, under the conditions used in the Examples, namely, when a culture chamber was tightly closed and the fraction was cultured in a DMEM medium containing 1.0 g/L glucose under an oxygen-free atmosphere, the oxygen concentration in the low oxygen chamber decreased to less than 1% in 1 hr and to 0.1-0.4% in 4 hr and was maintained throughout the experiment. Culturing under OGD for 24 hr caused cell death, culturing under OGD for 18 hr did not cause cell death by the evaluation based on propidium iodide assay and lactate dehydrogenase assay. Detection of M2 microglia started 12 hr after starting OGD culture, increased to the maximum in 24 hr and thereafter decreased markedly. Therefore, the OGD treatment for about 18 hr (e.g., 18±6 hr) under the above-mentioned conditions is desirable.

In the present invention, the "low oxygen concentration" preferably means a concentration that mimics the oxygen concentration in the local cerebral infarct and is, for example, less than 1%, more preferably 0.1-0.4%. Culturing at a low oxygen concentration exceeding 1% (e.g., 2-10%) has been reported to be effective for maintenance of undifferentiated state of ES cells and improvement of iPS cell establishment efficiency. However, a preferable oxygen depletion (OD) treatment in the present invention is performed under severe low oxygen conditions causing cell death of microglia and monocyte after 24 hr. The low oxygen conditions can be created by, for example, replacing the atmosphere in the culture chamber with an oxygen-free inert gas such as 5% $CO_2$-containing nitrogen gas and the like.

In the present invention, the "low sugar concentration" preferably means a concentration that mimics the sugar concentration in the local cerebral infarct and is, for example, not more than 1.0 g/L. To provide the effect of the present invention, a sugar concentration of not more than 1.0 g/L is sufficient, and lowering sugar concentration more than necessary may sometimes prove undesirable for cell survival. The low sugar conditions can be created by, for example, culturing a cell population containing microglia or monocytes in a medium having the low sugar concentration. As the medium, a well-known conventionally-used basal medium such as Eagle's medium, minimum essential medium (MEM), Dulbecco's modified Eagle medium (DMEM), RPMI medium (e.g., RPMI1630, RPMI1640), Fischer's medium, ham medium (e.g., F10, F12), MCDB medium (e.g., MCDB104, MCDB107) and the like or a mixed medium thereof can be used. Depending on the sugar concentration of each basic medium, the medium is used after reducing the amount of sugar to be added as appropriate to meet the low sugar concentration in the present invention. In the case of DMEM, for example, low glucose medium (1.0 g/L) and high glucose medium (4.5 g/L) are commercially available. A low glucose medium can be selected for use. A glucose-free medium is also commercially available, and sugar may be added thereto to a desired low sugar concentration. The sugar is not particularly limited as long as microglia and monocyte can utilize, and glucose, galactose, fructose and the like, generally glucose, can be used.

The above-mentioned basal medium may additionally contain well-known conventionally-used medium additives such as 5-20% of serum (e.g., fetal bovine serum) or serum replacement (e.g., Knockout Serum Replacement), growth factor (e.g., EGF, PDGF, IGF-I, IGF-II, insulin, IL-1, IL-6), albumin, transferrin, protease inhibitor (e.g., α1-antitrypsin), cell adhesion factor (e.g., fibronectin, laminin), lipid (e.g., cholesterol, linoleic acid, steroid), trace element (iron, zinc, selenous acid, manganese, copper) and the like. The present invention can impart sufficient angiogenesis and/or axon outgrowth promoting ability to microglia and monocyte even without adding animal-derived components such as serum, growth factor and the like. In a preferable embodiment, as a medium, a medium substantially consisting of basal medium alone and free of serum or growth factor can be used. Since the medium does not contain expensive components derived from animals that are at risk of contamination with viruses or the like, an inexpensive and safe cell preparation can be provided.

Summarizing the conditions of these OGDs, the low oxygen concentration is an oxygen concentration of less than 1%, the low sugar concentration is a sugar concentration of not more than 1.0 g/L, and the culture period is less than 24 hr. When monocyte or peripheral blood mononuclear cell fraction is used, the culture period is preferably set to 18 hr or below.

A cell culture obtained as mentioned above can be used as it is or formulated with a pharmaceutically acceptable carrier. Examples of the pharmaceutically acceptable carrier include aqueous liquids for injection such as saline, isotonic solution containing glucose or other auxiliary agent (e.g., D-sorbitol, D-mannitol, sodium chloride and the like) and the like. A cell preparation containing the cell culture of the present invention may contain, for example, buffering agent (e.g., phosphate buffer, sodium acetate buffer), soothing agent (e.g., benzalkonium chloride, procaine hydrochloride and the like), stabilizer (e.g., human serum albumin, polyethylene glycol and the like), preservative, antioxidant and the like.

As shown in the below-mentioned Examples, cultures obtained by OGD treatment of a cell population containing microglia or monocytes characteristically have properties of
(a) significantly high secretion amount of VEGF,
(b) significantly high secretion amount of MMP-9, and
(c) significantly high secretion amount of TGF-β
compared to cultures treated under normal oxygen concentration and sugar concentration conditions (or the cell population before OGD treatment). Since VEGF, MMP-9 and TGF-β have an angiogenesis and axon outgrowth promoting action, administration of a culture obtained by OGD treatment can induce regeneration of neural tissue damaged or destroyed by ischemia or bleeding.

In addition, cultures obtained by OGD treatment of a cell population containing microglia or monocytes further have properties of
(d) significantly high ratio of secretion amount of TGF-β to that of TNF-α, and/or
(e) significantly low secretion amount of IL-6
compared to cultures treated under normal oxygen concentration and sugar concentration conditions (or the cell population before OGD treatment). That is, preferential secretion of anti-inflammatory cytokine than inflammatory cytokine can provide an inflammation suppressive effect at the site of ischemia/hemorrhage.

Therefore, a cell preparation containing a culture obtained by OGD treatment of a cell population containing microglia or monocytes can be used for treating ischemic cerebrovascular disease or ischemic cardiac disease, and is expected to promote angiogenesis and provide an anti-inflammatory action. The ischemic cerebrovascular disease in the present invention refers to what is called a cerebrovascular disease and includes cerebral infarction (cerebral thrombus, cerebral embolism), as well as hemorrhagic cerebral disorder (intracerebral bleeding, subarachnoid hemorrhage). A preferable application includes cerebral infarction. In addition, a cell preparation containing a culture obtained by OGD treatment of a cell population containing monocytes can also be used for ischemic diseases such as ischemic cardiac diseases (e.g., myocardial infarction) and the like. Alternatively, it can also be used for traumatic cerebrospinal neuropathy.

As a method for delivering the cell preparation produced by the method of the present invention to an affected part, for example, local transplantation by surgical means, intravenous administration, local injecting administration, subcutaneous administration, intradermal administration, intraperitoneal administration, intramuscular administration, intracerebral administration, intraventricular administration, intraarterial administration and the like are considered.

Transplantation by injection of cells into a patient when used for, for example, repair of the nervous system includes storing the cells to be transplanted in a syringe in a suspended state using artificial cerebrospinal fluid, saline or the like, exposing the neural tissue damaged by the surgery and injecting the cells directly into the injured site with an injection needle. The cells may also be transplanted to the vicinity of the injured site and the effect can also be expected by injection into the cerebrospinal fluid. Furthermore, the effect can also be expected by intravenous injection. Therefore, transplantation in the manner of ordinary transfusion becomes possible, which is preferable in that the transplantation operation in the hospital ward is possible.

The dose of the cell preparation of the present invention when, for example, PMNCs are intravenously administered to patients with cerebral infarction is $10^5$-$10^8$ cells, preferably $5 \times 10^5$-$10^7$ cells, in the number of mononuclear cells. The ratio of monocytes in mononuclear cells is estimated to be about 1/3 to 1/15. Therefore, as for the number of monocytes, a number obtained by multiplying the number of the above-mentioned mononuclear cells by the ratio is considered to be administered. The dose of microglia also includes the number of cells corresponding to the dose of monocytes.

EXAMPLE

The present invention is explained in detail in the following by referring to Example of the present invention. The present invention is not limited by the Example in any way. The following Example was carried out strictly in accordance with the recommendations of guidelines of the National Institutes of Health, USA, on the management and use of laboratory animals and was carried out after approval by the Niigata University Animal Experimentation Ethics Committee.

(Focal Cerebral Ischemia)

Transient focal cerebral ischemia was induced using male Sprague-Dawley rats (body weight 290-320 g) and silicone-coated nylon monofilament.

To be specific, rats were anesthetized by inhalation of 1.5% halothane in a mixture of 70% nitrous oxide and 30% oxygen. Nylon monofilament with diameter 0.148 mm was used for blood vessel obstruction. The tip of the nylon monofilament was rounded with heat. The end (11 mm) of the suture thread was coated with silicone (diameter 0.350 mm). The middle cerebral artery (MCA) was obstructed by inserting the embolic thread into the internal carotid artery via the external carotid artery. 90 min. after ischemia, the embolic thread was drawn to restore blood flow.

This resulted in the formation of a region of ischemic core and penumbra determined by the presence of microtubule-associated protein 2 (MAP2). In addition, the treatment time range for rescuing the tissues of penumbra by reperfusion was 90 minutes.

(Immunofluorescent Staining and Confocal Microscope)

Rats that survived 1 day, 3 days, 7 days, 14 days, and 28 days after cerebral ischemia were intracardially perfused with saline, perfused with cold 4% paraformaldehyde in cold 0.1 M phosphate buffered saline (PBS; pH 7.4) and euthanized by overdose of halothane.

The brains were removed and embedded in paraffin wax. Serial sections (4 μm thick) were cut out from paraffin blocks and stained with antibodies. Free floating sections were prepared (50 μm thick) and dyed. Nuclear staining was performed with vectashield 4',6'-diamidino-2-phenylindole (DAPI). Sections were examined under a confocal laser scanning microscope. Cerebral cortex tissue corresponding to ischemic core or penumbra was determined by MAP2 staining.

(Quantitative Analysis of Brain Tissue Structure by Immunostaining)

To perform quantitative analysis of brain tissue structure, tissue sections were immunostained with antibodies against cluster of differentiation (CD) 31 (marker for endothelial cell and angiogenesis), MAP2 (marker for dendrite of neuron), SMI31 and growth-associated protein 43 (GAP43) (neuronal axon marker), VEGF, TGF-β, and MMP-9 and counted.

(Primary Cultured Cells of Microglia)

Primary mouse microglia was collected. To be specific, after digesting cerebral cortex with papain, the cell suspension was cultured for 10 days in Dulbecco's modified Eagle medium (DMEM) supplemented with 10% fetal bovine serum (FBS) to isolate mixed glial cells from the cerebral cortex of postnatal C57BL/6 mice. After 10 days, the culture flask was shaken for 15 min to isolate microglia. Evaluation by Mac-1 (CD11b/CD18) immunoreactivity in flow cytometry showed that the purity of these microglia cultures was 99%.

(Peripheral Blood Mononuclear Cells)

Rat or human peripheral blood was mixed with PBS to a total volume of 35 mL, overlaid on 15 mL of ficoll (GE Healthcare Japan Ficoll-Paque Premium 1.084) in a 50 mL conical tube, centrifuged at 400×g for 30 min and the PMNC layer emerging on the ficoll layer was separated.

(OGD: Oxygen-Glucose Depletion Stimulation, OD: Oxygen Depletion Stimulation, GD: Glucose Depletion Stimulation)

For induction of OGD, first, the serum-containing medium was thoroughly washed twice with PBS to remove serum components. Then, the medium was replaced with a low sugar medium, a low oxygen chamber was replaced with a mixed gas of 95% $N_2$ and 5% $CO_2$ for 1 hr, and the chamber was closed for 18 hr thereafter. As the low sugar medium, DMEM (Dulbecco's modified Eagles medium) was used and the sugar concentration thereof was set to 1.0 g/L.

The oxygen concentration in the low oxygen chamber decreased to less than 1% in 1 hr, decreased to 0.1 to 0.4% in 4 hr and was maintained throughout the experiment.

OD was performed in the same manner as OGD except that serum-free high glucose (4.5 g/L) DMEM was used instead of low sugar medium. GD was performed in the same manner as OGD except that the atmosphere in the chamber was 5% $CO_2$, 95% atmosphere.

Culturing under OGD for 24 hr caused cell death, culturing under OGD for 18 hr did not cause cell death by the evaluation based on propidium iodide assay and lactate dehydrogenase assay. Detection of M2 microglia started 12 hr after starting OGD culture, increased to the maximum in 24 hr and thereafter decreased markedly. Therefore, in this Example, OGD for 18 hr was selected.

Microglia cultured under OGD is hereinafter referred to as OGD pre-treated microglia. Also, to compare with OGD pre-treated microglia, microglia cultured under a normal oxygen concentration (e.g., about 20%) is referred to as normal oxygen microglia.

(Cell Transplantation)

In this Example, to create the same physiological condition, rats with a mean body weight-2SD or lower were excluded on day 7 after cerebral ischemia. $1\times10^6$ microglia or $1\times10^5$ or $1\times10^6$ rat PMNCs were diluted with 300 μL of PBS. On day 7 after cerebral ischemia, rats subjected to transient MCAO (middle cerebral artery occlusion) were randomly assigned to the following groups. These groups are a cell-treated group consisting of rats transplanted with microglia or PMNCs slowly through the stump of the external carotid artery (ECA) for 3 min and a cell-free control group consisting of rats injected with the same volume of PBS. The cell-treated group includes an OGD pre-treated microglia- or PMNCs-transplanted group consisting of rats transplanted with OGD pre-treated microglia or PMNCs and a normal oxygen microglia- or PMNCs-transplanted group consisting of rats transplanted with normal oxygen microglia or PMNCs. The OGD pre-treated PMNCs-transplanted group includes a $1\times10^5$ PMNCs-transplanted group and a $1\times10^6$ PMNCs-transplanted group depending on the number of graft cells.

(Sensorimotor Evaluation)

Sensorimotor evaluation was performed before cerebral ischemia, and on day 1, day 4, day 7, day 10 (day 3 post-transplantation), day 14 (day 7 post-transplantation), day 21 (day 14 post-transplantation) and day 28 (day 21 post-transplantation) after cerebral ischemia by a corner test. In the corner test, the test was conducted 20 times in which rats escaped from the corner by turning to the left or right and the number of escape from the right was counted.

(Green Fluorescent Protein (GFP) Mouse)

To determine whether transplanted microglia can be transferred from blood to brain parenchyma to exert the beneficial effects thereof after intraarterial administration, primary microglia from GFP mouse was used in this Example. Primary microglia from GFP mouse was pre-treated with OGD, and the cells were intraarterially administered. Thereafter, confocal microscopic examination was performed on days 3 and 21 from the transplantation performed 7 days after cerebral ischemia.

(ELISA and Western Blot)

Human PMNCs were stimulated with OGD, GD or OD for 18 hr, and the cells and culture supernatant were separated. The cell extract and the culture supernatant were subjected to SDS-polyacrylamide electrophoresis, respectively, and VEGF was quantified by Western blot using a mouse anti-human VEGF antibody and a labeled anti-mouse IgG antibody. As the internal standard, β-actin (for cell extract) and transferrin (for culture supernatant) were respectively used. For the culture supernatant, quantification of VEGF by ELISA was also performed.

(Results)

The therapeutic effect of the transplantation of OGD pre-treated microglia on focal cerebral ischemia is explained.

To compare the therapeutic effects of the transplantation of OGD pre-treated microglia on focal cerebral ischemia, neurological outcome was analyzed between the cell-free control group and the OGD pre-treated microglia-transplanted group by sensorimotor evaluation after focal cerebral ischemia.

FIG. 1 shows one example of the improved results of neurological outcome after transplantation of OGD pre-treated microglia.

In the rats of the OGD pre-treated microglia-transplanted group, function recovery was greatly improved compared to the cell-free control group in the corner test conducted 20 times. That is, in the corner test conducted 20 times on day 28 after cerebral ischemia, the rats in the OGD pre-treated microglia-transplanted group turned to the right at a rate of about 50% and the rats in the cell-free control group turned to the right at a rate of about 10%. This indicates that the improvement of neuropathy was significantly better in the OGD pre-treated microglia-transplanted group than in the cell-free control group. Between these groups, no significant difference was found in the body weight before cerebral ischemia and on days 7, 14, 21 and 28 after cerebral ischemia.

Next, the therapeutic effect of the presence or absence of OGD pre-treatment on microglia was compared by the sensorimotor evaluation after focal cerebral ischemia.

Figure 2:
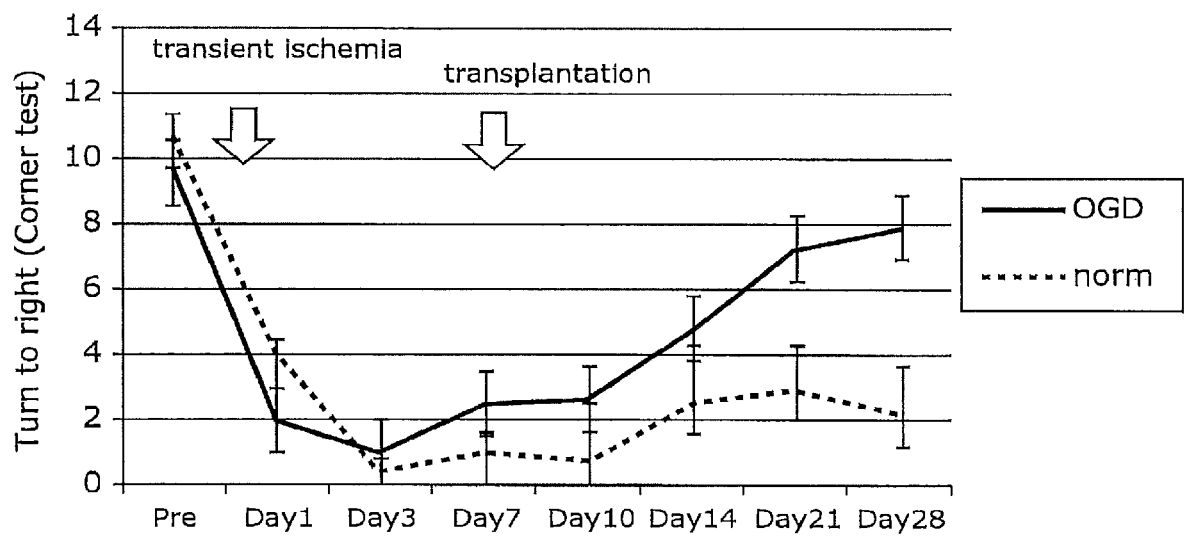
FIG. 2 shows other example of the improved results of neurological outcome in rat model of transient focal cerebral ischemia after transplantation of OGD pre-treated microglia.

FIG. 2 shows other example of the improved results of neurological outcome after transplantation of OGD pre-treated microglia.

Rats after transplantation of OGD pre-treated microglia showed drastically improved functional recovery compared to rats after transplantation of normal oxygen microglia (norm) in the corner test conducted 20 times. That is, in the corner test conducted 20 times on day 28 after cerebral ischemia, the rats in the OGD pre-treated microglia-transplanted group turned to the right at a rate of about 40% and the rats in the normal oxygen microglia-transplanted group turned to the right at a rate of about 10%. This indicates that the improvement of neuropathy was significantly better in the OGD pre-treated microglia-transplanted group than in the normal oxygen microglia-transplanted group. Between these groups, no significant difference was found in the body weight before cerebral ischemia and on days 7, 14, 21 and 28 after cerebral ischemia.

Here, by confocal microscopic examination, after intraarterial administration of microglia from GFP mouse, that is, on day 21 after transplantation, the microglia were not observed but observed in the boundary region between the ischemic core and penumbra on day 3 after transplantation. That is, it was confirmed by the confocal microscopic examination that microglia migrated from blood to brain parenchyma.

Figure 3:
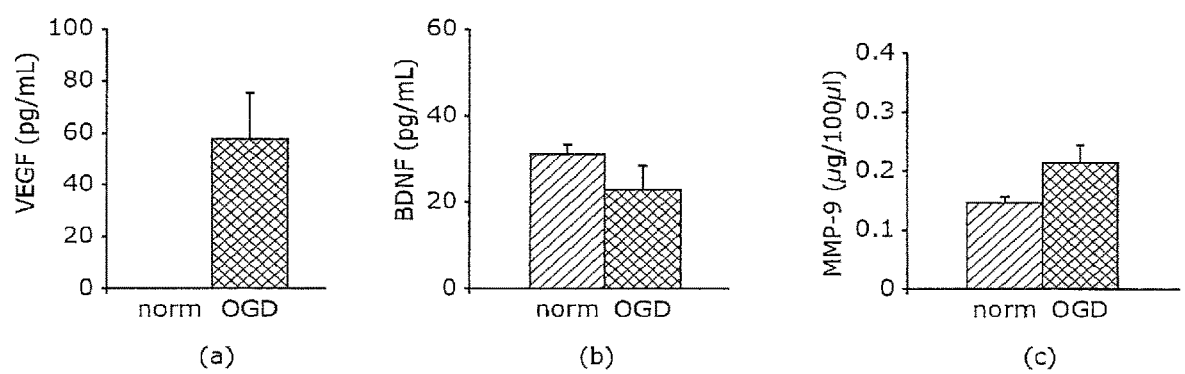
FIG. 3 shows properties of primary culture of mouse microglia pre-treated with OGD.

FIG. 3 shows properties of primary culture of mouse microglia pre-treated with OGD. To be specific, FIG. 3 shows the secretion levels from primary culture of mouse microglia under normal oxygen condition (norm) or OGD into the medium. FIG. 3 (a) shows secretion level of vascular endothelial growth factor (VEGF), (b) shows secretion level of brain-derived neurotrophic factor (BDNF), and (c) shows secretion level of MMP-9.

As shown in FIG. 3(a), the secretion level of VEGF in the medium of OGD pre-treated microglia was found to be markedly higher than the secretion level in that of normal oxygen microglia.

On the other hand, as shown in FIG. 3(b), there was no difference in the secretion level of BDNF between microglial media in OGD and normal oxygen states. However, as shown in FIG. 3(c), it was found that the secretion level of MMP-9 in the medium of OGD pre-treated microglia was higher than the secretion level in that of normal oxygen microglia.

Figure 4:
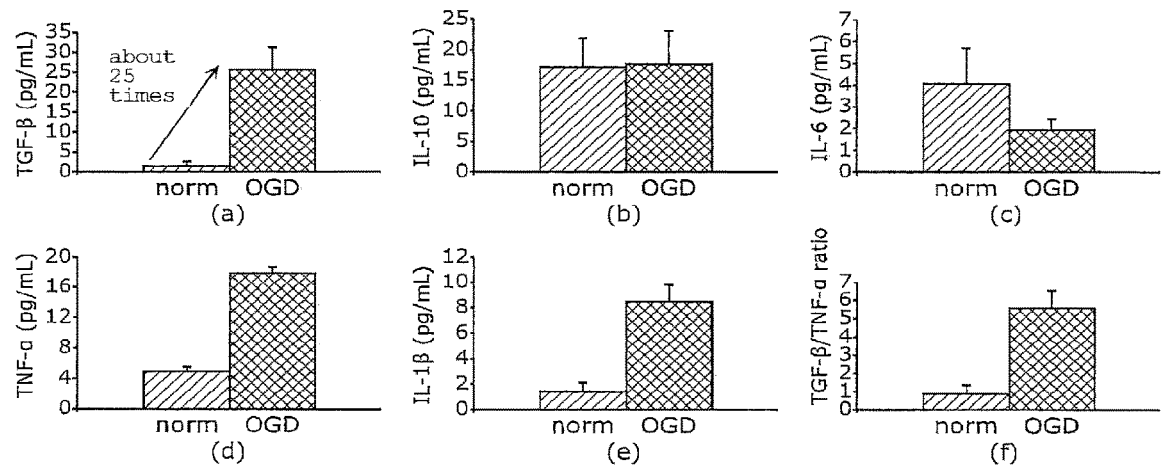
FIG. 4 shows other properties of primary culture of mouse microglia pre-treated with OGD.

FIG. 4 shows other properties of primary culture of mouse microglia pre-treated with OGD. To be specific, FIG. 4 shows, similar to FIG. 3, the secretion levels in the medium of primary culture of mouse microglia under normal oxygen state (norm) or OGD. FIGS. 4 (a) and (b) show secretion levels of anti-inflammatory cytokines such as transforming growth factor β (TGF-β) and interleukin 10 (IL-10). FIGS. 4(c), (d) and (e) show secretion levels of inflammatory cytokines such as IL-6, tumor necrosis factor α (TNF-α) and IL-1β. FIG. 4(f) shows the ratio of TGF-β to TNF-α.

To determine the change in cytokine profile of OGD pre-treated microglia, as shown in FIG. 4, the levels of several cytokines from microglia were compared between normal oxygen state and OGD. In general, M1 microglia secretes TNF-α, IL-1β, and IL-6, and brain protective M2 microglia secretes IL-10 and TGF-β.

As shown in FIG. 4(a), the secretion level of anti-inflammatory cytokine TGF-β by OGD pre-treated microglia is 25 times higher than that by normal oxygen microglia. As shown in FIG. 4(c), the secretion level of inflammatory cytokine IL-6 by OGD pre-treated microglia was found to be half that by normal oxygen microglia.

On the contrary, as shown in FIG. 4(b), the secretion levels of anti-inflammatory cytokine IL-10 by OGD pre-treated microglia and normal oxygen microglia showed no difference. On the other hand, as shown in FIGS. 4(d) and (e), the secretion levels of inflammatory cytokines TNF-α and IL-1β by OGD pre-treated microglia were 3 or 4 times higher than those by normal oxygen microglia.

As shown in FIG. 4(f), the ratio of TGF-β to TNF-α, which indicates the bias between M1 microglia and M2 microglia, from OGD pre-treated microglia was 6 times higher than that from normal oxygen microglia. The increase in the ratio of TGF-β to TNF-α indicates bias to M2 microglia after OGD pre-treatment. In other words, these results demonstrated that an optimal pre-treatment with OGD caused microglia to become anti-inflammatory M2 subtype dominant.

Next, expression of VEGF, MMP-9, and tGF-β by transplantation of OGD pre-treated microglia is explained.

Analysis was performed to confirm whether improved results after transplantation of OGD pre-treated microglia were caused by elevation of remodeling factors (VEGF, MMP-9, and TGF-β) in brain parenchyma. That is, using antibodies against VEGF, MMP-9 and TGF-β, immunohistochemical analysis of the brain of transplanted rats on day 28 post cerebral ischemia was performed. Expression of VEGF, MMP-9, and TGF-β could not be detected in rat brain before ischemia. The expression thereof was observed in the ischemic core and in the boundary region within penumbra on day 28 (day 21 after transplantation) after cerebral ischemia.

Figure 5:
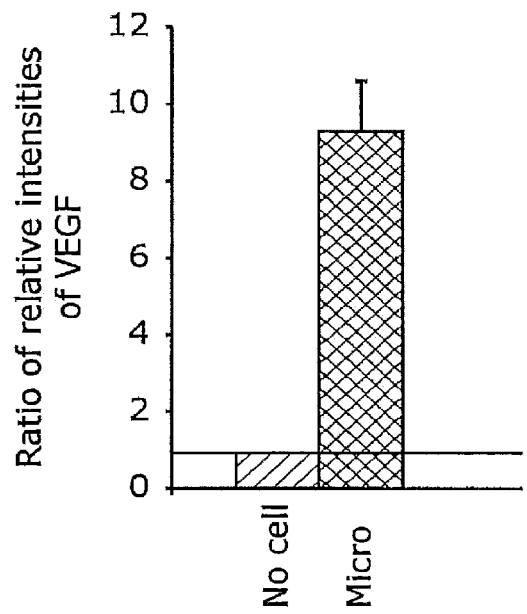
FIG. 5 shows intensity of VEGF on day 28 after cerebral ischemia, which is promoted by transplantation of OGD pre-treated microglia.
Figure 6:
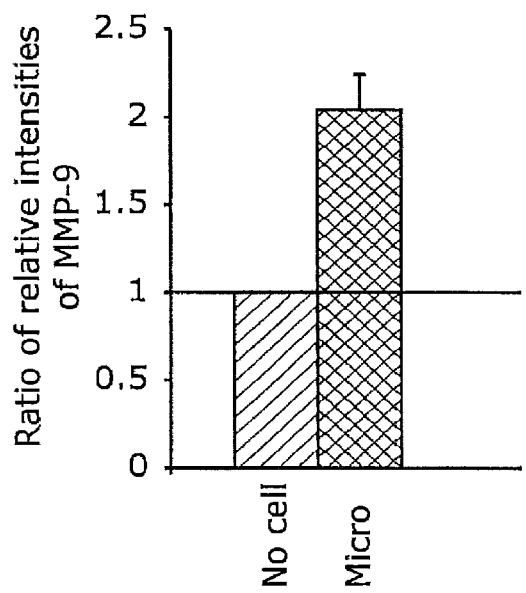
FIG. 6 shows intensity of MMP-9 on day 28 after cerebral ischemia, which is promoted by transplantation of OGD pre-treated microglia.
Figure 7:
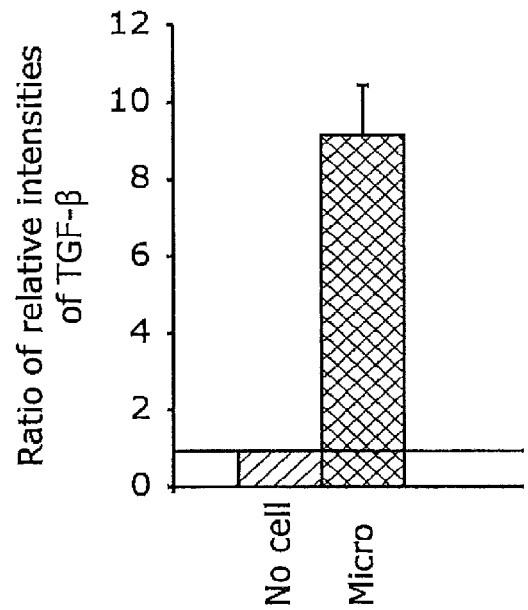
FIG. 7 shows intensity of TGF-β on day 28 after cerebral ischemia, which is promoted by transplantation of OGD pre-treated microglia.

FIG. 5-FIG. 7 show expression of various factors promoting remodeling on day 28 after cerebral ischemia, which is promoted by transplantation of OGD pre-treated microglia. FIG. 5 shows intensity of VEGF, FIG. 6 shows intensity of MMP-9, and FIG. 7 shows intensity of TGF-β.

The analysis of the intensity of immunoreactivity shown in FIG. 5-FIG. 7 demonstrated that expression of these remodeling factors was more pronounced in the OGD pre-treated microglia-transplanted group than in the cell-free control group.

Expression of VEGF and MMP-9 was observed not only in microglia but also pericytes, endothelial cells, and nerve cells in ischemic rats. Expression of TGF-β was observed not only in microglia but also pericytes and nerve cells in ischemia rats.

Then, it was confirmed that the transplantation of OGD pre-treated microglia promotes angiogenesis in the boundary region within the ischemic core and axon outgrowth in the ischemic penumbra on day 28 after cerebral ischemia.

First, promotion of angiogenesis by transplantation of OGD pre-treated microglia is explained.

The present inventors assumed that expression of VEGF, MMP-9, and TGF-β by the transplantation of OGD pre-treated microglia promotes angiogenesis. Thus, the present inventors examined the effect of transplantation of OGD pre-treated microglia on angiogenesis by immunofluorescent staining of cerebral cortex using angiogenesis marker anti-CD31 antibody on day 28 after cerebral ischemia.

Figure 8:
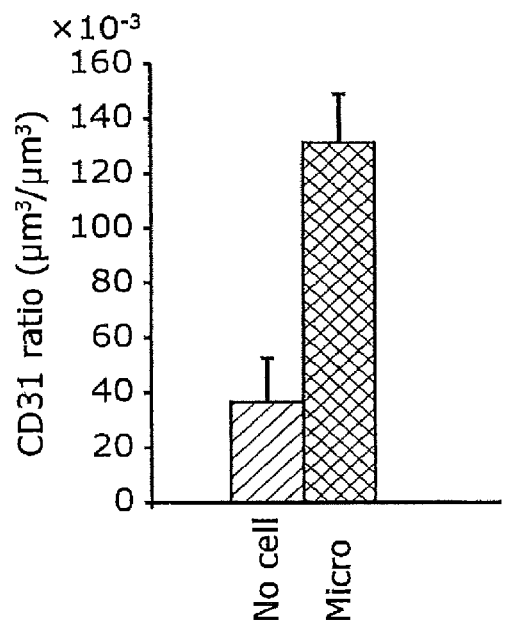
FIG. 8 shows immunoreactivity against CD31 (volume per unit volume).

FIG. 8 shows immunoreactivity against CD31 per unit volume. To be specific, the CD31 immunoreactivity is expressed as the volume ($\mu m^3$) per 1 $\mu m^3$ of the ischemic core of each of the cell-free control group and the OGD pre-treated microglia-transplanted group on day 28 after ischemia, that is, as the volume ratio.

In the evaluation by confocal microscope, as shown in FIG. 8, it was clarified that the immunoreactivity against CD31 in the OGD microglia-transplanted group was much more prominent than the CD31 immunoreactivity in the cell-free control group on day 28 after cerebral ischemia (day 21 after transplantation). The immunoreactivity against CD31 is the immunoreactivity against CD31 per unit volume in the boundary region containing the ischemic core. Between these groups, no significant difference was found in the immunoreactivity against CD31 per unit volume in the ischemic penumbra.

Next, promotion of axon outgrowth by the transplantation of OGD pre-treated microglia is explained.

The present inventors investigated the effect of the transplantation of OGD pre-treated microglia on axon outgrowth by immunofluorescent staining of the ischemic cortex using an anti-SMI 31 antibody against a protein marker for neurofilament on day 28 after cerebral ischemia.

FIG. 9 shows immunoreactivity against SMI31 per unit volume. To be specific, the CD31 immunoreactivity is expressed as the volume ($\mu m^3$) per 1 $\mu m^3$ of the ischemic penumbra of each of the cell-free control group and the OGD-microglia-transplanted group on day 28 after ischemia, that is, as the ratio.

Expression of SMI31 in the ischemic penumbra in the OGD pre-treated microglia-transplanted group was more prominent than the expression in the cell-free control group.

In the OGD pre-treated microglia-transplanted group, expression of other axon outgrowth marker GAP43 in the ischemic penumbra was more prominent than the expression in the cell-free control group. In contrast, between these groups, no significant difference was found in the expression of MAP2 in the ischemic penumbra.

To determine the mechanism by which transplantation of OGD pre-treated microglia promotes axon outgrowth, the present inventors evaluated expression of chondroitin sulfate proteoglycan (CSPG). This is because it inhibits axon outgrowth and is cleaved and degraded by MMP-9.

To confirm the assumption that an increase in MMP-9 expressed by the transplantation of OGD pre-treated microglia induces a decrease in expression of CSPG and leads to axon outgrowth, the present inventors performed immunofluorescent staining using anti-CSPG/NG2 antibody (NG2 is the main component of CSPG).

FIG. 10 shows relative intensities of chondroitin sulfate proteoglycan/neuron glial antigen 2 (CSPG/NG2) in cerebral cortexes to that in sham surgery rats on day 28 after ischemia. The cerebral cortexes include cortex of cell-free control group and cortex of OGD pre-treated microglia-transplanted group.

As shown in FIG. 10, the level of CSPG/NG2 was compared between transplanted rats on day 28 after cerebral ischemia and rats of the sham surgery group. In the evaluation by confocal microscope, it was clarified that the expression of CSPG/NG2 in the ischemic penumbra in the OGD pre-treated microglia-transplanted group was much lower than those in the sham surgery group and the cell-free control group on day 21 after transplantation (day 28 after cerebral ischemia).

Figure 11:
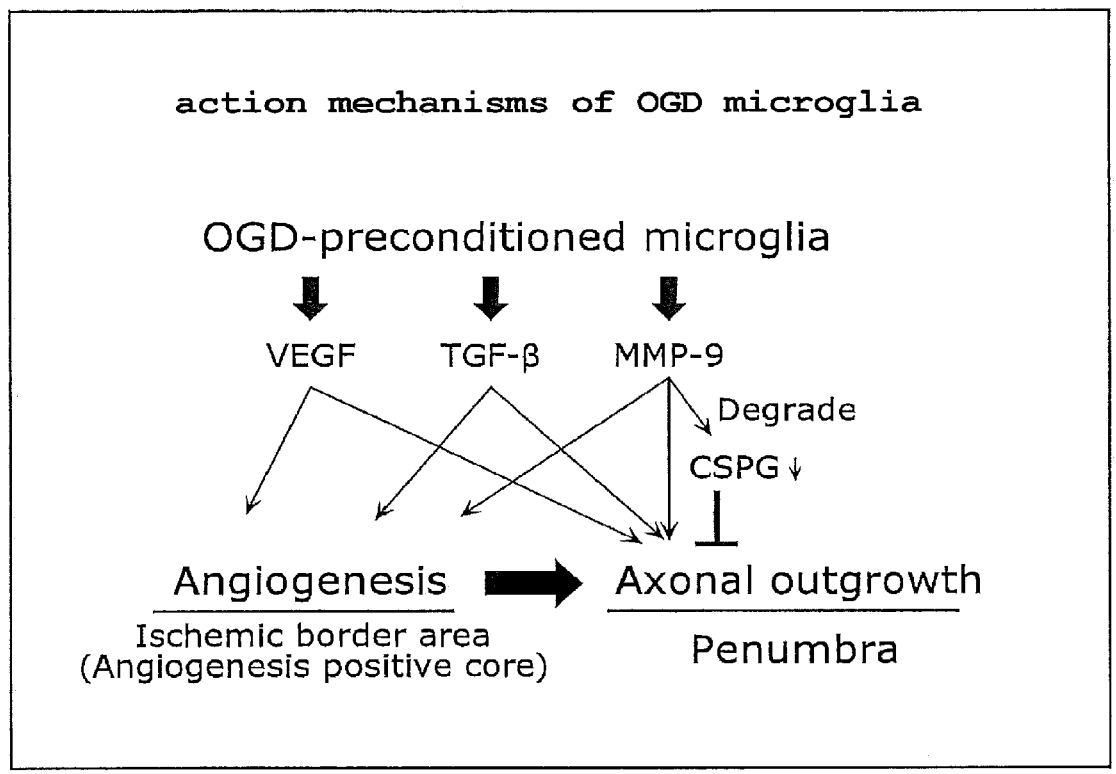
FIG. 11 shows the mechanisms in transplantation of OGD pre-treated microglia after cerebral ischemia.

FIG. 11 shows the mechanisms in transplantation of OGD pre-treated microglia after cerebral ischemia.

Transplantation of OGD pre-treated microglia causes direct secretion of VEGF, TGF-β, and MMP-9. These factors may be due to paracrine secreted by resident cells via remodeling factors secreted by OGD pre-treated microglia. These factors directly promote angiogenesis in the ischemic core. The ischemic core is defined as MAP2-immunologically negative site, which is composed of an irreversibly angiogenesis-negative ischemic core and an angiogenesis-positive ischemic core that shows angiogenesis.

MMP-9 from microglia decreases expression of an axon outgrowth inhibitory factor CSPG. Therefore, axon outgrowth can be induced easily. VEGF, TGF-β, and MMP-9 may directly induce axon outgrowth.

Monocytes pass from the cerebral vessel through BBB to the brain parenchyma and differentiate into microglia. Since monocytes can be easily collected from peripheral blood, they can be obtained less invasively than microglia. Thus, whether the same effect as microglia can be obtained by subjecting a peripheral blood mononuclear cell (PMNC) fraction containing monocytes to OGD treatment was verified by sensorimotor evaluation in a rat model of focal cerebral ischemia transplanted with rat PMNCs ($1 \times 10^6$).

Figure 13:
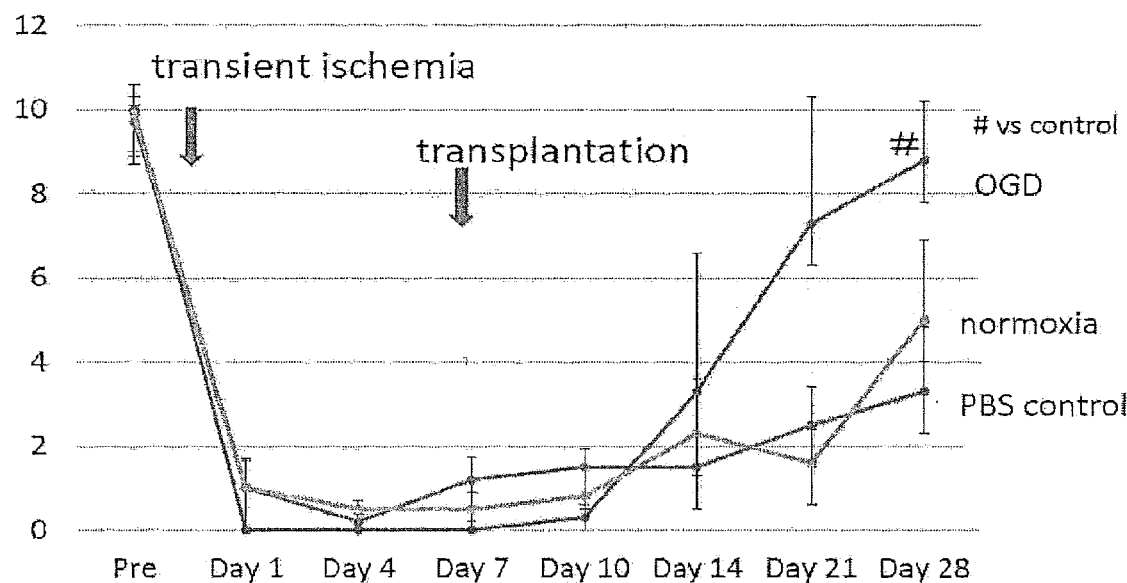
FIG. 13 shows one example of the improved results of neurological outcome in rat model of transient focal cerebral ischemia after transplantation of OGD pre-treated peripheral blood mononuclear cells (PMNCs). In the Figure, "#" shows $p<0.05$ relative to the control.

The results are shown in FIG. 13. No significant difference was found in the PMNC administration group without OGD stimulation (normoxia) from the cell non-administration group (PBS control), but significant symptomatic improvement was observed on day 28 after ischemia treatment in the OGD-stimulated PMNC administration group (OGD).

Next, the dependency of the effect of OGD stimulation on cell number was investigated by changing the number of PMNCs to be transplanted.

Figure 14:
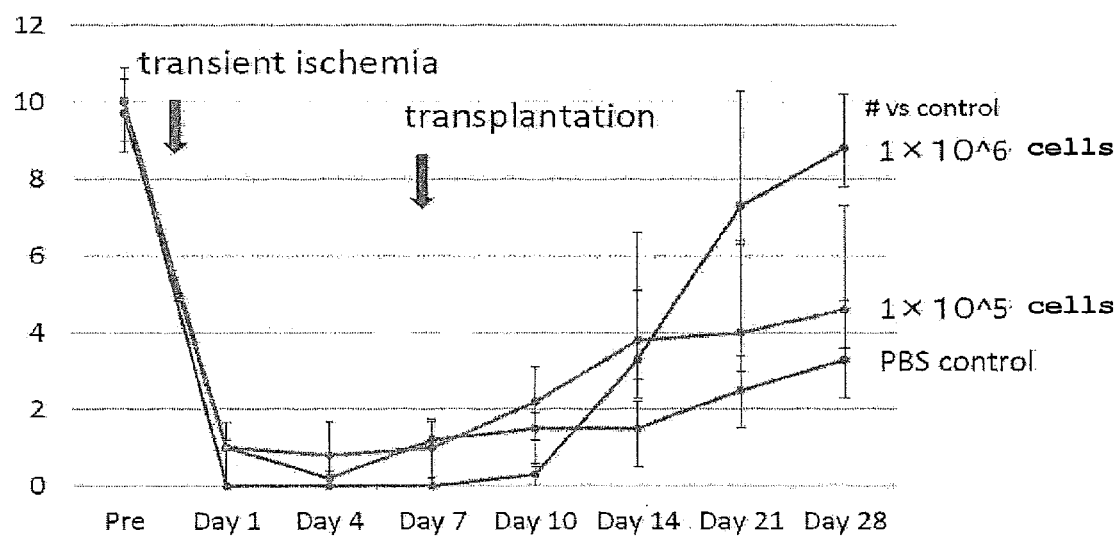
FIG. 14 shows dependency on the grafted cell number of OGD pre-treated PMNCs in the improvement of neurological outcome in rat model of transient focal cerebral ischemia. In the Figure, "#" shows $p<0.05$ relative to the control.

The results are shown in FIG. 14. In the OGD-stimulated PMNC administration group, significant symptomatic improvement was observed in a cell number-dependent manner on day 28 after the ischemia treatment.

Next, to evaluate angiogenesis and nerve axon outgrowth in cerebral ischemic lesions by the transplantation of OGD-stimulated PMNCs, immunohistochemical staining of the tissue sections of the lesion area and the vicinity thereof was performed. Anti-CD31 antibody was used for evaluation of angiogenesis, and anti-SMI31 antibody was used for evaluation of axon outgrowth, respectively, as a primary antibody.

Figure 15:
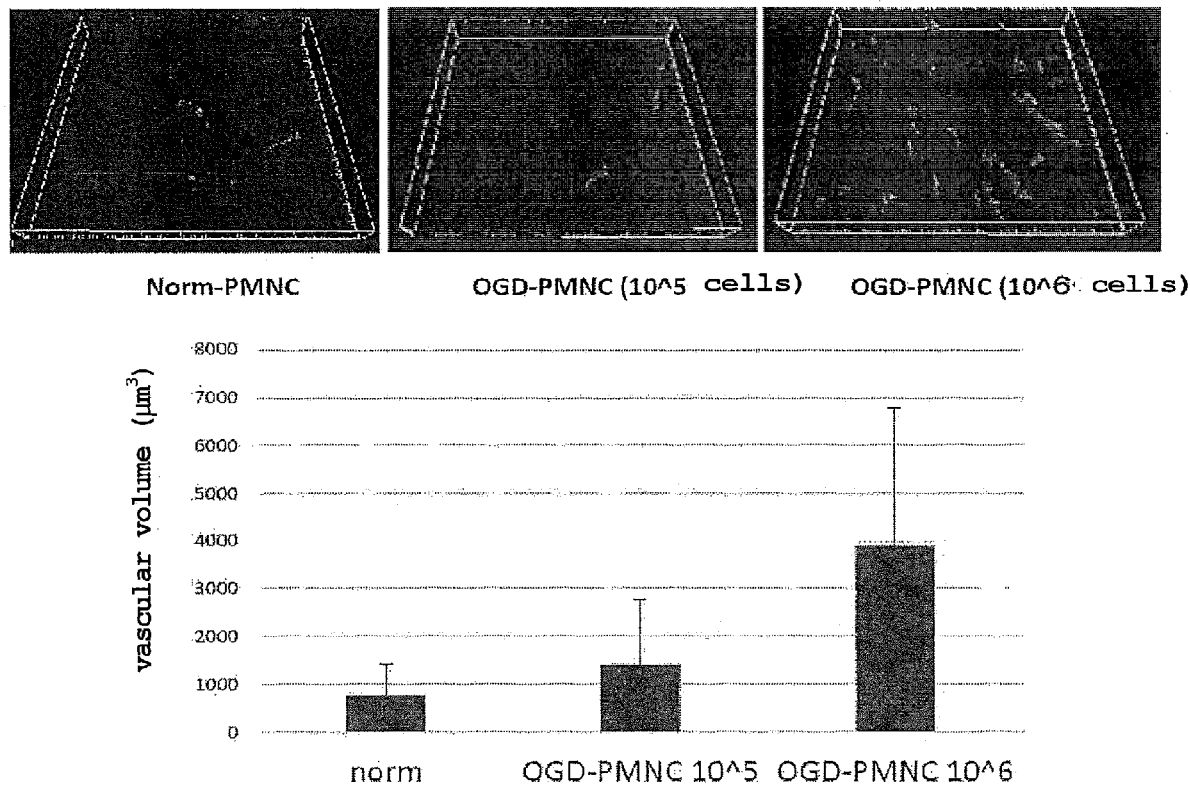
FIG. 15 shows promotion of angiogenesis in cerebral ischemia lesion of rat model of transient focal cerebral ischemia transplanted with OGD pre-treated PMNCs. The upper panel shows a double stained image of immunostaining of angiogenesis marker CD31 and nuclear staining by DAPI, and the lower panel is a graph showing vascular volume calculated from the staining results.
Figure 16:
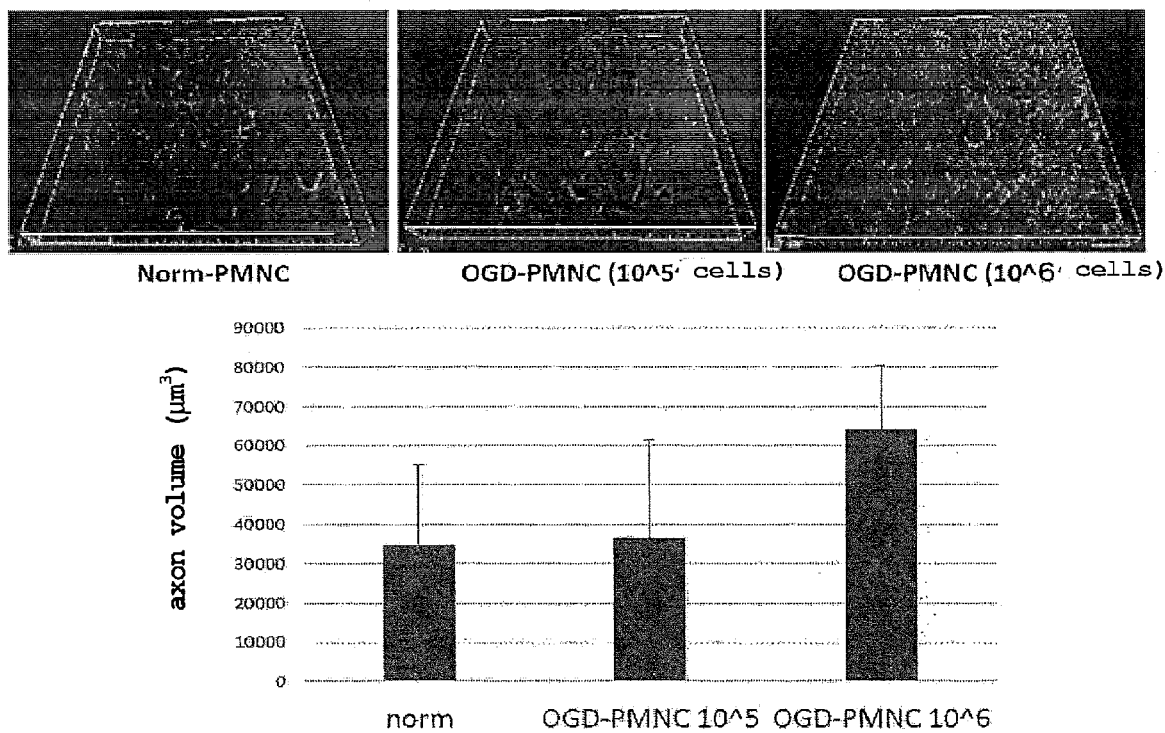
FIG. 16 shows promotion of nerve axon outgrowth in cerebral ischemia lesion of rat model of transient focal cerebral ischemia transplanted with OGD pre-treated PMNCs. The upper panel shows a double stained image of immunostaining of nerve axon marker SMI31 and nuclear staining by DAPI, and the lower panel is a graph showing nerve axon volume calculated from the staining results.

The results are shown in FIGS. 15 and 16. The $1 \times 10^6$ OGD-stimulated PMNCs administration group (OGD-PMNC 10^6) showed significantly promoted angiogenesis and axon outgrowth compared to the PMNC administration group without OGD stimulation (norm).

Next, the superiority of OGD stimulation to oxygen-depletion stimulation only (OD) and glucose depletion stimulation only (GD) was evaluated using human PMNCs and using the amounts of production and secretion of VEGF as an index. Human PMNCs were stimulated with OD, GD or OGD for 18 hr, and the amount of VEGF in the cells and the amount of VEGF in the culture supernatant (secretion amount) were quantified by Western blotting. For the culture supernatant, VEGF was also quantified by ELISA.

The results are shown in FIG. 17. The VEGF production amount of the cells tended to increase even with OD stimulation alone, compared to the PMNC administration group without OGD stimulation (norm). The level was higher with GD stimulation alone, OGD stimulation showed a higher level, and the VEGF production amount significantly increased relative to the PMNC administration group without OGD stimulation (norm). On the other hand, the amount of secretion into the medium did not show a remarkable difference from the control by OD stimulation alone, whereas a tendency toward increase was found relative to the control even by GD stimulation alone. The amount of VEGF secretion further increased by OGD stimulation, and it showed a significant difference from not only the control but also OD stimulation alone.

Next, an example of a treatment protocol for cerebral hemorrhage is shown in which microglia is isolated from destroyed white matter surrounding hematoma removed during hematoma removal surgery in patients with cerebral, hemorrhage, and the microglia is stimulated with OGD and retransplanted to the patient.

After aspiration removal of hematoma under neuroendoscopic observation, bleeding blood vessel is identified and hemostasis is performed. The hematoma cavity is washed, and the destroyed white matter is recovered with forceps. After dissociating the cells of the white matter, microglia is isolated by MACS or FACS using anti-CD 115 antibody. The obtained microglia is stimulated with OGD for 18 hr, $1 \times 10^6$ microglia is suspended in PBS and intravenously administered to patient.

(Summary)

As described above, in the above-mentioned Example, a cell preparation containing a culture for treating cerebral infarction, promoting angiogenesis, or promoting axon outgrowth could be produced by culturing a cell population containing microglia or monocytes under OGD conditions. In addition, the therapeutic effect could be improved by OGD.

As is clear from the Example using human PMNCs, to impart microglia and monocyte the ability to promote angiogenesis and/or axon outgrowth, it is only necessary to give the cell population a stimulus for bringing the cell population closer to an ischemic state. For this end, the cell population may be cultured under conditions of either low oxygen concentration or low sugar concentration. It is preferable to cultivate the cell population at least under the condition of low sugar concentration, and it is more preferable to cultivate the cell population under the condition of OGD, that is, under the condition of low oxygen concentration and low sugar concentration.

As is clear from the Example using rat and human PMNCs, since monocyte transferred from blood vessel to brain parenchyma becomes microglia, a cell population containing monocytes together with or instead of microglia may be cultured under the condition of OGD. When the cell population contains monocytes, the cell population may be a fraction containing peripheral blood cell or cell fraction thereof, for example, mononuclear cells collected from peripheral blood. Since it is not necessary to collect bone marrow fluid for the production of a cell preparation, the burden on the patient in treating cerebral infarction can be reduced and the safety can be enhanced. In the case of the above-mentioned patent document 1, since mesenchymal stem cells are recovered, a sufficient number of the cells cannot be obtained and it is necessary to proliferate the cells, which not only increases the culture period but also requires a special facility such as a cell processing center (CPC) and the like. In the present invention, however, since monocytes can be easily collected from peripheral blood, proliferation is not necessary, the culture time can be shortened, and graft cells can be prepared in a medical institution that performs transplantation without CPC.

In the above-mentioned Example, an angiogenesis and axon outgrowth promoting activity sufficient for brain function recovery in a rat cerebral ischemia model could be conferred to microglia and PMNCs by, in OGD, reducing the oxygen concentration in a low oxygen chamber to less than 1% in 1 hr and to 0.1-0.4% in 4 hr, and maintaining the concentration. This means that an average oxygen concentration in a culture atmosphere of less than 1% to 0.4% is sufficient to achieve the effect of the present invention. Similarly, in the above-mentioned Example, the above-mentioned activity could be conferred to microglia and PMNCs by setting the sugar concentration to 1.0 g/L. This means that a sugar concentration in the medium of not more than 1.0 g/L is sufficient for affording the effect of the present invention.

In the above-mentioned Example, a cell population was cultured under OGD conditions for 18 hr. However, such culture period is one embodiment and may be less than 24 hr. This is because, as described above, M2 microglia increased maximally in 24 hr, then decreased markedly, and further caused cell death in 24 hr.

The cell preparation prepared according to the above-mentioned Example is typically a cell preparation for treating cerebral infarction. This cell preparation shows a therapeutic effect for not only cerebral infarction but also any ischemic disease as long as microglia or monocytes can reach the site of ischemia. For example, it also shows a therapeutic effect for myocardial infarction, pulmonary infarction, renal infarction and the like.

The method for producing a cell preparation according to one embodiment of the present invention may include washing of a culture or the like.

Figure 12:
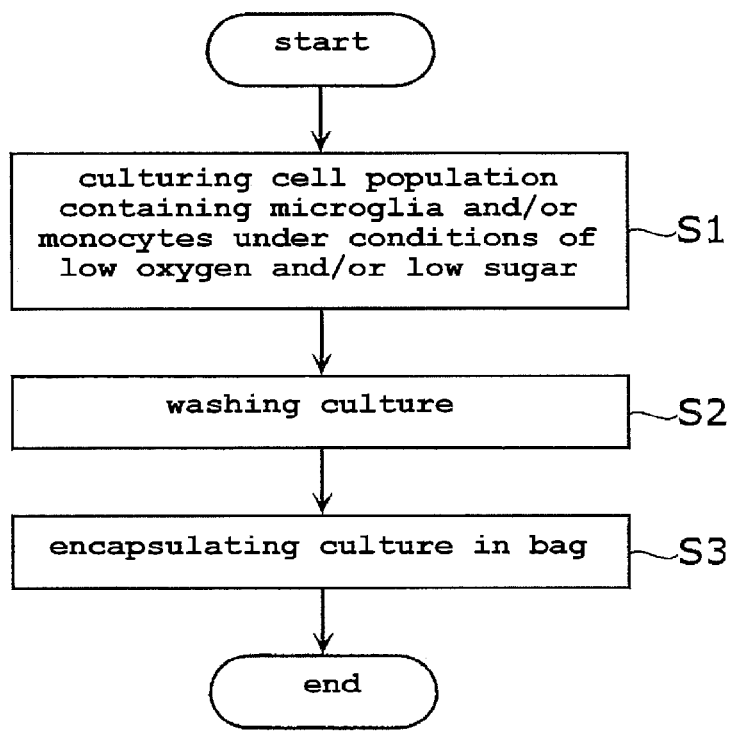
FIG. 12 is a flowchart showing a production method of a cell preparation.

FIG. 12 is a flowchart showing a production method of a cell preparation.

A culture is produced by culturing a cell population containing microglia and/or monocytes under conditions of low oxygen concentration and/or low sugar concentration (step S1). Then, the culture is washed (step S2). To be specific, granulocyte or debris killed by OGD is separated from the culture by centrifugal force and the culture is washed. Then, the culture is encapsulated in a bag to produce a cell preparation (step S3).

The present invention may also be a method for treating an ischemic disease (e.g., cerebral infarction) by administering a cell preparation produced by the flowchart of FIG. 12 to patients. In this case, in step S3 of FIG. 12, for example, about $1\times10^8$ cells are encapsulated in a 40 mL bag. Transplantation is performed by administering the cell preparation intravenously for, for example, 30 min to 1 hr. The cell preparation may be administered not only intravenously but also intraarterially, intracerebrally or the like.

Also, lumbar puncture administration, intracerebral administration, intraventricular administration or local administration may be used.

In the method of treating human, peripheral blood is collected from a patient and a cell population including monocytes is separated from the peripheral blood before step S1 shown in FIG. 12. That is, the cell population is a fraction containing monocytes collected from the peripheral blood. Alternatively, the cell population is a fraction containing mononuclear cells collected from peripheral blood. Then, a cell preparation is produced by culturing the cell population under conditions of OGD and administered to the patient. In this case, the burden on a person as a patient is extremely small, and an effect of high safety is afforded. Also, it is not necessary to grow monocytes and addition of a drug is not necessary. Furthermore, since the culture period is short, treatment is possible from early stages of onset. In addition, therapeutic effects are expected even when some time has passed since the onset. Furthermore, this treatment is done at a low cost, and also effective even by intravenous administration.

In a method of treating animals other than human, before step S1 shown in FIG. 12, as shown in the above-mentioned Example (primary cell culture), for example, microglia is collected from the brain of animal other than human and a cell population containing the microglia is cultured under conditions of OGD. A cell preparation is produced by the culturing, and administered to an animal other than human as a patient. In the present specification, when simply indicated as a patient, the patient means a human and a non-human animal.

The culture contained in the cell preparation produced according to the above-mentioned Example is microglia and/or monocytes cultured under the conditions of OGD. Microglia or monocytes cultured in this way cannot be specified as a structure or at least specifying as a structure is not practical even in consideration of the technical common knowledge at the time of filing. In the scope of the appended claims, therefore, the microglia or monocytes may be identified by a production method.

While the cell preparation according to one embodiment of the present invention, a method for producing the cell preparation and a treatment method thereof have been described based on the Example, the present invention is not limited to the Example. As long as the gist of the present invention is not deviated, the Example variously modified by those of ordinary skill in the art may also be included in the present invention. Also, all publications and patent documents cited herein are hereby incorporated in their entirety by reference.

INDUSTRIAL APPLICABILITY

The cell preparation of the present invention is remarkably effective for functional recovery of ischemic diseases, and utilizable as a medicament for the diseases.

The invention claimed is:
1. A method for the promotion of angiogenesis and axon outgrowth in a subject, comprising administering to the subject a composition comprising a therapeutically effective amount of autologous microglia and/or monocytes, wherein the autologous microglia and/or monocytes are obtained by;
   culturing the microglia and/or monocytes in the presence of oxygen at a concentration of 1% or less and glucose at a concentration of 1.0 g/L or less for a period of

12-24 hours, thereby obtaining microglia and/or monocytes with the ability to promote angiogenesis and axon outgrowth; and wherein the composition is administered to the subject by intravenous administration, intraperitoneal administration, intracerebral administration, intraventricular administration, intraarterial administration, or local transplantation.

2. A method for the treatment of an ischemic cerebrovascular disease, traumatic brain injury, or spinal cord injury in a subject, comprising administering to the subject a composition comprising a therapeutically effective amount of autologous microglia and/or monocytes, wherein the autologous microglia and/or monocytes are obtained by;

culturing the microglia and/or monocytes in the presence of oxygen at a concentration of 1% or less and glucose at a concentration of 1.0 g/L or less for a period of 12-24 hours, thereby obtaining microglia and/or monocytes with the ability to promote angiogenesis and axon outgrowth; and wherein the composition is administered to the subject by intravenous administration, intraperitoneal administration, intracerebral administration, intraventricular administration, intraarterial administration, or local transplantation.

3. The method of claim 1, wherein the composition is administered to the subject by intravenous administration.

4. The method of claim 2, wherein the composition is administered to the subject by intravenous administration.

5. The method of claim 1, wherein the monocytes are collected from peripheral blood.

6. The method of claim 1, wherein the monocytes are isolated from a fraction comprising mononuclear cells collected from peripheral blood.

7. The method of claim 1, wherein the low oxygen concentration is an oxygen concentration of 0.1 to 0.4%.

8. The method of claim 1, wherein the culture period is about 18 hr.

9. The method of claim 2, wherein the monocytes are collected from peripheral blood.

10. The method of claim 2, wherein the monocytes are isolated from a fraction comprising mononuclear cells collected from peripheral blood.

11. The method of claim 2, wherein the low oxygen concentration is an oxygen concentration of 0.1 to 0.4%.

12. The method of claim 2, wherein the culture period is about 18 hr.

* * * * *